United States Patent
Qi et al.

(10) Patent No.: US 12,024,790 B2
(45) Date of Patent: *Jul. 2, 2024

(54) QUALITY PREDICTION METHOD, PREPARATION METHOD AND SYSTEM OF CONDUCTIVE GALLIUM OXIDE BASED ON DEEP LEARNING AND CZOCHRALSKI METHOD

(71) Applicant: HANGZHOU FUJIA GALLIUM TECHNOLOGY CO. LTD., Zhejiang (CN)

(72) Inventors: Hongji Qi, Hangzhou (CN); Duanyang Chen, Hangzhou (CN); Qinglin Sai, Hangzhou (CN)

(73) Assignee: HANGZHOU FUJIA GALLIUM TECHNOLOGY CO. LTD., Hangzhou (CN)

( * ) Notice: Subject to any disclaimer, the term of this patent is extended or adjusted under 35 U.S.C. 154(b) by 142 days.

This patent is subject to a terminal disclaimer.

(21) Appl. No.: 17/761,042

(22) PCT Filed: Feb. 5, 2021

(86) PCT No.: PCT/CN2021/075570
§ 371 (c)(1),
(2) Date: Mar. 16, 2022

(87) PCT Pub. No.: WO2022/141752
PCT Pub. Date: Jul. 7, 2022

(65) Prior Publication Data
US 2023/0160097 A1 May 25, 2023

(30) Foreign Application Priority Data
Dec. 31, 2020 (CN) .......................... 202011640679.2

(51) Int. Cl.
C30B 15/20 (2006.01)
C30B 29/16 (2006.01)
G06N 3/082 (2023.01)

(52) U.S. Cl.
CPC .............. C30B 15/20 (2013.01); C30B 29/16 (2013.01); G06N 3/082 (2013.01)

(58) Field of Classification Search
CPC ......... C30B 15/20; C30B 15/14; C30B 29/16; C30B 15/34; G16C 20/30; G16C 20/70; G16C 20/10
See application file for complete search history.

(56) References Cited

U.S. PATENT DOCUMENTS 11,489,090 B1 * 11/2022 Atanackovic ..... H01L 21/02433
11,502,223 B1 * 11/2022 Atanackovic ............ H01S 5/32
(Continued)

FOREIGN PATENT DOCUMENTS

CN 103247518 A 8/2013
CN 106868593 A 6/2017
(Continued)

OTHER PUBLICATIONS

Office Action issued on Jun. 5, 2023, in corresponding Japanese Application No. 2022522836, 8 pages.
(Continued)

*Primary Examiner* — Robert M Kunemund
(74) *Attorney, Agent, or Firm* — Maier & Maier, PLLC

(57) ABSTRACT

A quality prediction method, a preparation method and a system of conductive gallium oxide based on deep learning and Czochralski method. The quality prediction method includes the steps of obtaining preparation data of conductive gallium oxide single crystal prepared by Czochralski method. The preparation data includes a seed crystal data, an environmental data, and a control data. The environmental
(Continued)

data includes doping element concentration and doping element type; preprocessing the preparation data to obtain a preprocessed preparation data; preparing the preprocessed data is input to a trained neural network model, and a predicted quality data corresponding to the conductive gallium oxide single crystal is obtained through the trained neural network model, and the predicted quality data includes a predicted carrier concentration.

10 Claims, 3 Drawing Sheets

(56) References Cited

U.S. PATENT DOCUMENTS

| | | | |
|---|---|---|---|
| 2005/0203715 | A1 | 9/2005 | Tai et al. |
| 2005/0288812 | A1 | 12/2005 | Cheng et al. |
| 2021/0351321 | A1* | 11/2021 | Atanackovic ..... H01L 21/02414 |

FOREIGN PATENT DOCUMENTS

| | | |
|---|---|---|
| CN | 111005064 A | 4/2020 |
| CN | 111368434 A | 7/2020 |
| CN | 111695287 A | 9/2020 |
| JP | 2005235961 A | 9/2005 |
| JP | 2011190127 A | 9/2011 |
| JP | 2011190134 A | 9/2011 |

OTHER PUBLICATIONS

International Search Report mailed Oct. 11, 2021, in corresponding to International Application No. PCT/CN2021/076071; 3 pages.
First Office Action issued Nov. 1, 2021, corresponding to Chinese Application No. 202011640679.2; 16 pages (with English Translation).

* cited by examiner

QUALITY PREDICTION METHOD, PREPARATION METHOD AND SYSTEM OF CONDUCTIVE GALLIUM OXIDE BASED ON DEEP LEARNING AND CZOCHRALSKI METHOD

CROSS-REFERENCE TO RELATED APPLICATIONS

This application is a national application of PCT Patent Application No. PCT/CN2021/075570, filed on Feb. 5, 2021, which claims priority to Chinese Patent Application No. 202011640679.2, filed on Dec. 31, 2020. The content of all of which is incorporate herein by reference.

FIELD

The disclosure relates to the field of gallium oxide single crystal preparation, in particular to a quality prediction method, a preparation method and a system for conductive gallium oxide based on a deep learning and a Czochralski method.

BACKGROUND $\beta$-$Ga_2O_3$ ($\beta$-Gallium oxide) is a direct band gap wide forbidden gap semiconductor material, the forbidden gap width is about 4.8~4.9 eV. It has many advantages such as large band gap, fast saturated electron drift speed, high thermal conductivity, high breakdown field strength, stable chemical properties, etc. It has a wide range of application prospects in the field of high-temperature, high-frequency, and high-power power electronic devices. In addition, the material can also be used for LED chips, solar-blind ultraviolet detection, various sensor components and imaging components, etc.

The Czochralski method is one of the methods for preparing conductive gallium oxide. In the prior art, when the conductive gallium oxide is prepared by the Czochralski method, the preparation parameters of conductive gallium oxide are difficult to control, and there are too many factors affecting the performance of conductive gallium oxide products, the conductive gallium oxide with the predetermined carrier concentration cannot be obtained.

Therefore, the existing technology needs to be improved and developed.

SUMMARY

Regarding the defects in the prior art described above, a quality prediction method, a preparation method and system of conductive gallium oxide based on deep learning and Czochralski method are provided, to solve the problem that the process of preparing conductive gallium oxide single crystal by Czochralski method depends on the operator's experience to set parameters, the repeatability is poor, and the conductive gallium oxide single crystal with a predetermined carrier concentration cannot be produced stably.

The technical solution of the present application to solve the technical problems is as follows:

A quality prediction method of conductive gallium oxide based on deep learning and Czochralski method, comprises the steps:

obtaining a preparation data of a conductive gallium oxide single crystal prepared by the Czochralski method, the preparation data includes a seed crystal data, an environmental data, and a control data, and the environmental data includes a doping element concentration and a doping element type;

preprocessing the preparation data to obtain a preprocessed preparation data;

inputting the preprocessed preparation data into a trained neural network model, and obtaining a predicted quality data corresponding to the conductive gallium oxide single crystal through the trained neural network model, and the predicted quality data includes a predicted carrier concentration.

In the quality prediction method of conductive gallium oxide based on deep learning and Czochralski method, the step of preprocessing the preparation data to obtain the preprocessed preparation data comprises:

obtaining the preprocessed preparation data according to the seed crystal data, the environmental data, and the control data, and the preprocessed preparation data is a matrix formed by the seed crystal data, the environmental data, and the control data.

In the quality prediction method of conductive gallium oxide based on deep learning and Czochralski method, the seed crystal data includes a half-height width of seed crystal diffraction peak, a deviation value of the half-height width of seed crystal diffraction peak and a seed crystal diameter;

the environmental data also includes a thermal resistance value of a upper insulation cover, a deviation value of the thermal resistance value of the upper insulation cover, a shape factor of a crystal growth channel, a shape factor of a crystal growth observation hole, a thermal resistance value of a lower insulation cover, and a deviation value of the thermal resistance value of the lower thermal insulation cover, a relative height between the crucible and the induction coil, and a relative height between the heating ring and the induction coil;

the control data includes a heating power, a cooling power, an atmosphere type, a cavity pressure, a gas flow rate, a seed crystal rod Czochralski speed, a crystal rotation speed, a crystallizing rate, and a crystal to crucible diameter ratio.

In the quality prediction method of conductive gallium oxide based on deep learning and Czochralski method, the step of obtaining preprocessed preparation data according to the seed crystal data, the environmental data, and the control data, comprises:

determining a preparation vector according to the seed crystal data, the environmental data, and the control data; a first element in the preparation vector is one of the half-height width of seed crystal diffraction peak, the deviation value of the half-height width of seed crystal diffraction peak and the seed crystal diameter; a second element in the preparation vector is one of a concentration of a doping element, a type of the doping element, a thermal resistance value of the upper insulation cover, the deviation value of the thermal resistance value of the upper insulation cover, the shape factor of the crystal growth channel, the shape factor of the crystal growth observation hole, the thermal resistance value of the lower insulation cover, the deviation value of the thermal resistance value of the lower insulation cover, the relative height between the crucible and the induction coil, and the relative height between the heating ring and the induction coil; a third element in the preparation vector is one of the heating power, the cooling power, the atmosphere type, the cavity pressure, the gas flow rate, the seed rod Czochralski speed, the crystal rotation speed, the crystallization rate, and the crystal to crucible diameter ratio;

determining the preprocessed preparation data according to the preparation vector.

In the quality prediction method of conductive gallium oxide based on deep learning and Czochralski method, wherein the predicting quality data further comprises: a predicted crack data, a predicted hybrid crystal data, a half-height width of predicted diffraction peak, a radial deviation value of the half-height width of predicted diffraction peak, a axial deviation value of the half-height width of predicted diffraction peak, a radial deviation value of the predicted load of carrier concentration, and an axial deviation value of the predicted carrier concentration.

In the quality prediction method of conductive gallium oxide based on deep learning and Czochralski method, wherein the trained neural network model is trained by the following training steps:

obtaining a training data and corresponding an actual quality data for preparing conductive gallium oxide single crystal by the Czochralski method, the training data includes a seed crystal training data, an environmental training data, and an control training data;

preprocessing the training data to obtain preprocessed training data;

inputting the preprocessed training data into a preset neural network model, and obtaining a predicted training generated quality data corresponding to the preprocessed training data through the preset neural network model;

adjusting and correcting model parameters of the preset neural network model according to the predicted training generated quality data and the actual quality data to obtain a trained neural network model.

In the quality prediction method of conductive gallium oxide based on deep learning and Czochralski method, the preset neural network model comprises a feature extraction module and a fully connected module, the step of inputting the preprocessed training data into a preset neural network model, and obtaining the predicted training generated quality data corresponding to the preprocessed training data through the preset neural network model includes:

inputting the preprocessed training data into the feature extraction module, and obtaining a feature vector corresponding to the preprocessed training data through the feature extraction module;

inputting the feature vector is input to the fully connected module, and obtaining the predicted training generated quality data corresponding to the preprocessed training data through the fully connected module.

A preparation method of conductive gallium oxide based on deep learning and Czochralski method, comprises the steps:

acquiring a target quality data of a target conductive gallium oxide single crystal, where the target quality data includes a target carrier concentration;

determining the target preparation data corresponding to the target conductive gallium oxide single crystal according to the target quality data and the trained neural network model, the target preparation data includes a target seed data, a target environment data, and a target control data, the target environment data includes a target doping element concentration and a target doping element type;

preparing, based on the Czochralski method, the target conductive gallium oxide single crystal according to the target preparation data.

In the preparation method of conductive gallium oxide based on deep learning and Czochralski method, the determining the target preparation data corresponding to the target conductive gallium oxide single crystal according to the target quality data and the trained neural network model, includes the steps:

acquiring a preset preparation data, preprocessing the preset preparation data, and obtaining the preprocessed preset preparation data;

inputting the preprocessed preset preparation data into a trained neural network model, and obtaining a predicted quality data corresponding to the preprocessed preset preparation data through the trained neural network model;

correcting the preset preparation data according to the predicted quality data and the target quality data to obtain the target preparation data corresponding to the target conductive gallium oxide single crystal.

A conductive gallium oxide preparation system based on deep learning and Czochralski method, comprises a memory and a processor, and a computer program stored in the memory, and the processor executes the computer program to operate the steps of the prediction method, or the steps of the preparation method.

Beneficial effects: the present application proposes a quality prediction method of conductive gallium oxide based on deep learning and Czochralski method and a preparation method. By preprocessing a preparation data of a conductive gallium oxide single crystal prepared by the Czochralski method to obtain a preprocessed preparation data, and then inputting the preprocessed preparation data into the trained neural network model, and obtain the predicted quality data corresponding to the conductive gallium oxide single crystal through the trained neural network model. The application can predict the quality of the conductive gallium oxide single crystal through the trained neural network model, so the preparation data can be adjusted to prepare the conductive gallium oxide single crystal with a predetermined carrier concentration.

BRIEF DESCRIPTION OF THE DRAWINGS

In order to explain the embodiments of the present application or the technical solutions in the prior art more clearly, the following will briefly introduce the drawings that need to be used in the description of the embodiments or the prior art. Obviously, the drawings in the following description are only some of the embodiments recorded in the present disclosure. For those of ordinary skill in the art, other drawings can be obtained based on these drawings without innovative work.

DETAILED DESCRIPTION OF THE EMBODIMENTS

The present disclosure provides a method and system for preparing conductive gallium oxide based on deep learning and Czochralski method. In order to make the objectives, technical solutions and effects of the present invention clearer and more specific, the present invention will be further described in detail below with reference to the drawings and examples. It should be understood that the specific embodiments described here are only used to explain the present invention, but not used to limit the present invention.

Those skilled in the art can understand that, unless specifically stated otherwise, the singular forms "a", "an", "said" and "the" used herein may also include plural forms. It should be further understood that the term "comprising" used in the specification of the present disclosure refers to the presence of the described features, integers, steps, operations, elements and/or components, but does not exclude the presence or addition of one or more other features, integers, steps, operations, elements, components, and/or groups of them. It should be understood that when we refer to an element as being "connected" or "coupled" to another element, it can be directly connected or coupled to the other element, or intervening elements may also be present. In addition, "connected" or "coupled" used herein may include wireless connection or wireless coupling. The term "and/or" as used herein includes all or any unit and all combinations of one or more of the associated listed items.

Those skilled in the art can understand that, unless otherwise defined, all terms (including technical and scientific terms) used herein have the same meanings as those commonly understood by those of ordinary skill in the art to which the present disclosure belongs. It should also be understood that terms such as those defined in general dictionaries should be understood to have a meaning consistent with the meaning in the context of the prior art, and unless specifically defined as here, they will not be idealized or overly explain the formal meaning.

In the following, the content of the disclosure will be further explained through the description of the embodiments in conjunction with the accompanying drawings.

Czochralski method is a traditional crystal growth method. When the Czochralski method is adopted to grow crystals, raw materials in a crucible are melted by heating, the melt temperature is accurately adjusted, and then a seed crystal is immersed in the melt. At the same time, an appropriate speed is applied in pulling and rotating to induce the melt to crystallize in the crucible. When crystals are grown by Czochralski method, there are high requirements for the design of temperature field, the stability of heating power and the experience of operators.

Figure 1:
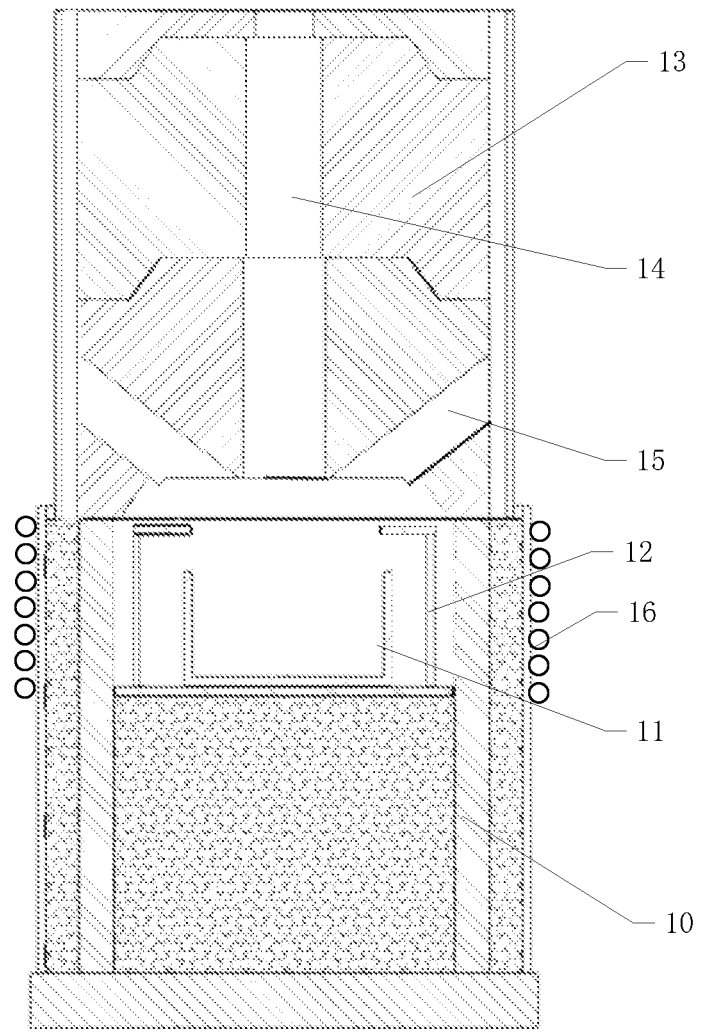
FIG. 1 is a schematic structural diagram of a crystal growth furnace for preparing a gallium oxide single crystal by a Czochralski method provided by the present application.

The present application provides a crystal growth furnace for growing conductive gallium oxide single crystals by Czochralski method, as shown in FIG. 1, it includes a lower insulation cover 10, a crucible 11 arranged in the lower insulation cover 10, and a heating ring 12 arranged outside of the crucible 11; an upper insulation cover 13 is provided inside a crystal growth channel 14, and a side of the upper insulation cover is provided with crystals in a growth observation hole 15, an induction coil 16 is also provided on a periphery of the lower insulation cover 10.

Based on the crystal growth furnace, conductive gallium oxide single crystals can be prepared. Firstly, the crystal growth furnace for preparing conductive gallium oxide single crystals is installed, including a material selection of the upper insulation cover, an axial opening size of the upper insulation cover, a shape and a size of the opening window, a material selection of the lower insulation cover, a relative position of the crucible to the induction coil, a relative position of the heating ring and the induction coil, etc., the above factors will affect a thermal field distribution inside the device, thereby affecting the conductive gallium oxide single crystal electrical conductivity. Furthermore, the type of doping element and the doping concentration are also key factors that affect the conductivity of conductive gallium oxide.

Putting the specific orientation β-$Ga_2O_3$ seed crystal into the seed crystal fixture, binding and fixing it, the orientation of the seed crystal may be [010], [001] direction, etc.; firstly, vacuuming an equipment through turning on a mechanical pump and a diffusion pump in turn, when the vacuum of the equipment is reached to a predetermined degree, turning off a vacuum equipment and slowly inflating into the crystal growth furnace according to a volume ratio of the mixed gas; then, by setting the heating power, the crucible is heated by the heating ring to completely melt the gallium oxide raw materials and doping element materials placed in the crucible; then, slowly descending the seed rod to immerse the seed crystal into the melt, and at the same time pull and rotate at a suitable speed to induce the melt crystallization in the crucible to obtain conductive gallium oxide single crystal, in this process, the lower insulation cover and the upper insulation cover are used to maintain the stable thermal field during the crystal growth process. In the process of preparing conductive gallium oxide single crystal, the heating power, a cooling power, an atmosphere type, a cavity pressure, an atmosphere cooling water flow, a seed rod Czochralski speed, crystal rotation speed, etc. The above factors will all affect product performance of the gallium oxide single crystal.

Figure 2:
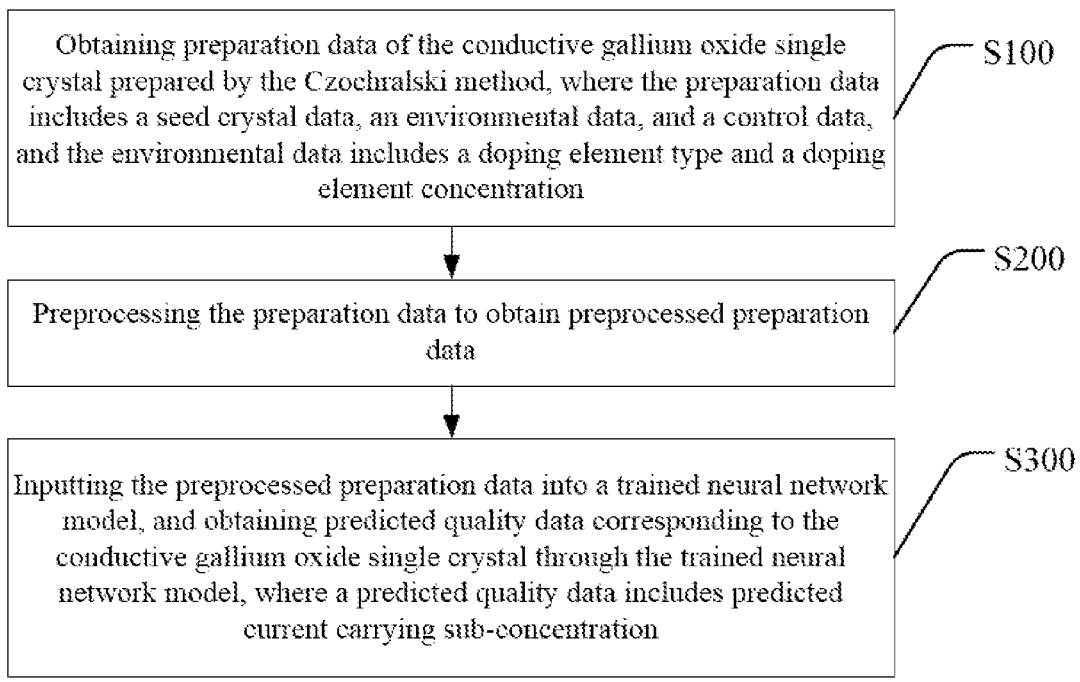
FIG. 2 is a flowchart of an embodiment of a quality prediction method of conductive gallium oxide based on deep learning and a Czochralski method provided by the present application.

Based on above, the present embodiment provides a quality prediction method of conductive gallium oxide based on deep learning and the Czochralski method, as shown in FIG. 2, which includes the following steps:

S100. Obtaining preparation data of the conductive gallium oxide single crystal prepared by the Czochralski method, where the preparation data includes a seed crystal data, an environmental data, and a control data, and the environmental data includes a doping element type and a doping element concentration.

The preparation data refers to the data of the conductive gallium oxide single crystal prepared by the Czochralski method, and the preparation data is the data that can be configured as required, for example, when it needs to predict the performance of the conductive gallium oxide single crystal obtained under a certain preparation data, it is only necessary to determine the preparation data, and preprocess the preparation data to obtain the preprocessed preparation data, and then input the preprocessed preparation data into the trained neural network model, and pass the trained neural network model. The network model obtains the predicted quality data, that is, no experiment is required. After the preparation data is determined, the quality data of the conductive gallium oxide single crystal can be predicted through the trained neural network model.

In this embodiment, the preparation data includes seed crystal data, environmental data, and control data. The seed crystal data refers to the data of the seed crystal used in the process of preparing the conductive gallium oxide single crystal by the Czochralski method. The environmental data refers to the data of the environment in which the crystal is placed in the process of preparing the conductive gallium oxide single crystal by the Czochralski method, and the control data refers to the control of crystal growth during the process of preparing the conductive gallium oxide single crystal by the Czochralski method. The concentration of the doping element is the concentration of the doping element in the conductive gallium oxide, and the type of the doping element includes Si, Ge, Sn, Zr, Hf, In, Ta, Nb, V, W, Mo, etc.

S200: Preprocessing the preparation data to obtain preprocessed preparation data.

After the preparation data is obtained, the preparation data is first preprocessed to obtain the preprocessed preparation data, so that the preprocessed preparation data can be input into the trained neural network model to pass the trained neural network, in order to the network model processes the pre-processed data.

In an implementation of the embodiment of the present application, step S200, preprocessing the preparation data to obtain the preprocessed preparation data includes:

S210: Obtaining preprocessed preparation data according to the seed crystal data, environmental data, and control data, where the preprocessed preparation data is a matrix formed by the seed crystal data, environmental data, and control data.

After the preparation data is obtained, the preparation data is preprocessed first to obtain the preprocessed preparation data. The sub-data (such as the seed crystal data, the environmental data, and the control data) in the preparation data will affect each other, but it is currently not clear how much the sub-data affects each other. Therefore, it is necessary to carry out the preparation data. Preprocessing, rearranging and combining the sub-data in the preparation data to form the preprocessed preparation data.

In another embodiment of the present application, the seed crystal data includes: half-height width of seed crystal diffraction peak, deviation value of the half-height width of seed crystal diffraction peak, and seed crystal diameter; the environmental data further includes: doping element type, doping element concentration, thermal resistance value of the upper insulation cover, deviation value of the thermal resistance value of the upper insulation cover, shape factor of the crystal growth channel, shape factor of the crystal growth observation hole, thermal resistance value of the lower insulation cover, and deviation value of the thermal resistance value of the lower insulation cover, the relative height between the crucible and the induction coil, and the relative height between the heating ring and the induction coil; the control data includes: a heating power, a cooling power, atmosphere type, a cavity pressure, gas flow, a seed rod Czochralski speed, a crystal rotation speed, a crystallization rate, and a ratio of crystal to crucible diameter.

The half-height width of seed crystal diffraction peak can be tested with an X-ray diffractometer. The deviation value of the half-height width of the seed crystal diffraction peak includes the radial deviation value of the half-height width of seed crystal diffraction peak and the axial deviation value of the half-height width of seed crystal diffraction peak, the radial direction is the direction on the horizontal plane, and the axial direction is the direction perpendicular to the horizontal plane, that is, the axis in the vertical direction. The radial deviation value of the half-height width of seed crystal diffraction peak can be measured by measuring the half-height width of seed crystal diffraction peak in the radial direction of the seed crystal, and the difference between the half-height width of seed crystal diffraction peak in the radial direction of the seed crystal can be obtained, namely the radial deviation value of the half-height width of seed crystal diffraction peak can be obtained. The axial deviation value of the half-height width of seed crystal diffraction peak can be measured by testing the half-height width of seed crystal diffraction peak on the seed crystal axis, and the difference between the half-height width of seed crystal diffraction peak on the seed crystal axis can be obtained. Then the axial deviation of the half-height width of seed crystal diffraction peak can be obtained. The seed crystal diameter can be directly measured.

As described above, when the conductive gallium oxide single crystal is prepared by using the crystal growth furnace shown in FIG. 1, the upper and lower insulation cover both provide a stable thermal field for the growth of the conductive gallium oxide single crystal. The thermal resistance value of the upper insulation cover refers to the temperature difference between the inner and outer sides of the insulation cover when the unit heat per unit time passes through the upper insulation cover. The larger the thermal resistance value of the upper thermal insulation cover, the stronger the ability of the upper thermal insulation cover to resist heat transfer, and the better the thermal insulation effect of the upper insulation cover.

The deviation value of the thermal resistance value of the upper insulation cover includes the radial deviation value of the thermal resistance value of the upper insulation cover and the axial deviation value of the thermal resistance value of the upper insulation cover. The radial deviation value of the thermal resistance value of the upper insulation cover can be measured by measuring the thermal resistance value of the upper insulation cover on both sides of the upper insulation cover in the radial direction, and the difference between the thermal resistance values of the upper insulation cover on the radial sides of the upper insulation cover can be obtained. Then the radial deviation value of the thermal resistance value of the upper insulation cover can be obtained. The axial deviation value of the thermal resistance value of the upper insulation cover can be measured by testing the thermal resistance value of the upper insulation cover on both sides of the upper insulation cover, and the difference between the thermal resistance values of the upper insulation cover on the axial sides of the upper insulation cover can be obtained. Then the axial deviation value of the thermal resistance value of the upper insulation cover can be obtained.

Similarly, the same method can be used to obtain the thermal resistance value of the lower insulation cover and the deviation value of the thermal resistance value of the lower insulation cover. The deviation value of the thermal resistance value of the lower insulation cover includes the radial deviation value of the thermal resistance value of the lower insulation cover and the axial deviation value of the thermal resistance value of the lower insulation cover.

The crystal growth channel shape factor refers to the value of the shape and size of the crystal growth channel. For example, when the crystal growth channel is cylindrical, the crystal growth channel shape factor includes: the diameter and height of the crystal growth channel; When the channel is a cube, the crystal growth channel shape factor includes a length, a height and a width of the crystal growth channel; the crystal growth channel shape factor also affects the thermal field distribution of the crystal growth environment, thereby affecting the crystal growth performance.

The crystal growth observation hole shape factor also refers to the value of the shape and size of the crystal growth observation hole, and the shape of the crystal growth observation hole also affects the thermal field distribution of the crystal growth environment, thereby affects the crystal growth performance.

Since the crucible is heated by the induction coil and the heating ring, the relative height between the crucible and the induction coil, and the relative height between the heating ring and the induction coil will affect the thermal field distribution of the crystal growth environment.

With the use of the crystal growth furnace for growing gallium oxide single crystals, the thermal resistance of the upper insulation cover, the thermal resistance of the lower insulation, the deviation of the thermal resistance of the upper insulation, and the deviation of the thermal resistance of the lower insulation may change, but it wouldn't change in short time. and the environmental data can be retested after a certain number of crystal growths.

The heating power refers to the heating power of the heating ring to the crucible, the cooling power refers to the power used to cool the environment in the crystal growth furnace using liquid, and the atmosphere type refers to the type of gas introduced into the crystal growth furnace, including $O_2$, Ar, $N_2$, $CO_2$, etc., the cavity pressure refers to the pressure in the crystal growth furnace, the gas flow refers to the gas flow into the crystal growth furnace, and the seed rod Czochralski speed refers to the speed at which the seed rod is pulled upward during the crystal growth process, the crystal rotation speed refers to the speed at which the seed rod drives the crystal to rotate during the crystal growth process, and the crystallization rate refers to the ratio of raw material to form crystals melting the gallium oxidation, and the ratio of crystal to crucible diameter refers to the ratio of the diameter of the produced crystal to the diameter of the crucible. These parameters are the control parameters that affect the crystal preparation by the Czochralski method.

In an implementation of this embodiment, step S210 of obtaining preprocessed preparation data according to the seed crystal data, environmental data, and control data includes:

S211. Determining a preparation vector according to the seed crystal data, the environmental data, and the control data; wherein the first element in the preparation vector is one of the half-height width of seed crystal diffraction peak, the deviation value of the half-height width of seed crystal diffraction peak, and one of the seed crystal diameters; the second element in the preparation vector is one of the concentration of the doping element, the type of the doping element, the thermal resistance of the upper insulation cover, the deviation value of the thermal resistance of the upper insulation cover, the shape factor of the crystal growth channel, the crystal growth observation hole shape factor, the thermal resistance value of the lower insulation cover, the deviation value of the thermal resistance value of the lower insulation cover, the relative height between the crucible and the induction coil, and the relative height between the heating ring and the induction coil; the third elements in the preparation vector are one of the heating power, cooling power, atmosphere type, cavity pressure, gas flow rate, seed crystal rod Czochralski speed, crystal rotation speed, crystallization rate, and crystal to crucible diameter ratio;

S212. Determining the preprocessed preparation data according to the preparation vector.

According to the seed crystal data A, the environmental data B, and the control data C, the preparation vector (A, B, C) is determined. The seed crystal data A is selected from the half-height width of seed crystal diffraction peak A1, the half-height width of seed crystal diffraction peak deviation value A2, and the seed crystal diameter A3. the environmental data B is selected from: the thermal resistance value of the upper insulation cover B1, the deviation value of the thermal resistance value of the upper insulation cover B2, the shape factor of the crystal growth channel B3, the shape factor of the crystal growth observation hole B4, the thermal resistance value of the lower insulation cover B5, the deviation value of the thermal resistance value of the lower insulation cover B6, the relative height between the crucible and the induction coil B7, the relative height between the heating ring and the induction coil B8, the doping element type B9 and the doping element concentration B10. The control data C is selected from the heating power C1, the cooling power C2, the atmosphere type C3, the cavity pressure C4, the gas flow C5, the seed crystal rod Czochralski speed C6, the crystal rotation speed C7, the crystallization rate C8, and the crystal to the crucible diameter ratio C9. In other words, A in the preparation vector (A, B, C) can be one of A1, A2, A3, and B can be one of B1, B2, B3, B4, B5, B6, B7, B8, B9, B10, C can be one of C1, C2, C3, C4, C5, C6, C7, C8, C9. Then 270 preparation vectors can be formed.

After all preparation vectors are arranged according to the sequence numbers to form a matrix, the preprocessed preparation data is obtained.

The preprocessed preparation data are as follows:

$$\begin{bmatrix} (A1B1\,C1) & \ldots & (A1B7\,C1)(A2\,B1\,C1) & \ldots & (A2B7\,C1)(A3B1\,C1) & \ldots & (A3B10C1) \\ \vdots & \ddots & & & & \ddots & \\ (A1B1\,C9) & \ldots & (A1B7\,C9)(A2\,B1\,C9) & \ldots & (A2B7\,C9)(A3B1\,C9) & \ldots & (A3B10\,C9) \end{bmatrix}$$

Of course, other arrangements are also used to obtain preprocessed preparation data.

S300. Inputting the preprocessed preparation data into a trained neural network model, and obtaining predicted quality data corresponding to the conductive gallium oxide single crystal through the trained neural network model, where a predicted quality data includes predicted current carrying sub-concentration.

The predicted quality data also includes a predicted crack data, a predicted hybrid crystal data, a half-height width of predicted diffraction peak, a radial deviation value of the half-height width of predicted diffraction peak, a axial deviation value of the half-height width of predicted diffraction peak, a radial deviation value of the predicted load of carrier concentration and an axial deviation value of the predicted carrier concentration. Among them, a crack data refers to a crack level data, and a predicted crack data refers to a predicted crack level data. For example, the cracks can be divided into multiple levels. For example, if the cracks are divided into 3 levels, the crack data are 1, 2 and 3.

A hybrid crystal data refers to a hybrid crystal level data, and a predicted hybrid crystal data refers to a predicted hybrid crystal level data. For example, a hybrid crystal can be divided into multiple levels. For example, the hybrid crystal is divided into 3 levels, and the hybrid crystal data are 1, 2 and 3 respectively.

A predicted half-height width of the diffraction peak refers to a predicted half-height width of the diffraction peak, the radial deviation value of the predicted half-height width of a diffraction peak refers to a predicted difference in the half-height width of the diffraction peak in the radial direction, and the deviation value of the predicted half-height width of the diffraction peak refers to a predicted difference in the half-height width of the diffraction peak in the axial direction.

A predicted carrier concentration refers to a number of electrons or holes per cubic centimeter. A carrier concentration is the main factor determining the conductivity of a semiconductor, and the unit is atom/cm$^3$. A predicted carrier concentration radial deviation value refers to a predicted difference of the carrier concentration in the radial direction, and a predicted axial deviation of the carrier concentration refers to the predicted difference of the carrier concentration in the axial direction.

In some embodiments, the trained neural network model is obtained by using the following training steps:

S01. Obtaining training data of the conductive gallium oxide single crystal prepared by the Czochralski method and corresponding actual quality data, where the training data includes the seed crystal training data, the environmental training data, and the control training data.

The training data refers to the data of the conductive gallium oxide single crystal prepared by the Czochralski method and used for training, and the actual quality data refers to the data of the actual quality of the conductive gallium oxide single crystal prepared by the Czochralski method. A training set is formed through training data and actual quality data, and a preset neural network model is trained based on the training set to obtain a trained neural network model.

When the training set is obtained by collecting data, the conductive gallium oxide single crystal is prepared by the Czochralski method, and the data for preparing the conductive gallium oxide single crystal is recorded as the training data. After the conductive gallium oxide single crystal is obtained, the quality the conductive gallium oxide single crystal is analyzed to obtain the actual quality data. In order to facilitate the training of the neural network model, as much data as possible can be collected to form the training set.

S02. Preprocessing the training data to obtain preprocessed training data.

After the training data is obtained, the training data is preprocessed to obtain the preprocessed training data. The preprocessing process may refer to step S200.

S03. Inputting the preprocessed training data into a preset neural network model, and obtaining a predicted training generated quality data corresponding to the preprocessed training data through the preset neural network model.

The preprocessed training data is input into the preset neural network model, and the predicted training generated quality data is obtained through the preset neural network model. A predicted training generated quality data includes: a predicted training generated crack data, a predicted training generated hybrid crystal data, a predicted training generated half-height width of diffraction peaks, a predicted training generated radial deviation of half-height width of diffraction peaks, and a predicted training generated axial deviation of half-height width of diffraction peaks.

S04. According to the predicted training generated quality data and the actual quality data, adjusting and correcting the model parameters of the preset neural network model to obtain a trained neural network model.

According to a prediction training and the actual quality data, the model parameters of the preset neural network model is corrected, and it is continued to execute the input of the preprocessed training data into the preset neural network model, to obtain the step of predicting training generating quality data corresponding to the preprocessed training data through the preset neural network model (that is, step S03), until a preset training conditions are met, and the trained neural network model is obtained.

According to the prediction training and the actual quality data, the model parameters of the preset neural network model is corrected, and it is continued to execute the input of the preprocessed training data into the preset neural network model, obtaining steps of the predicted training generating quality data corresponding to the preprocessed training data through the preset neural network model, until the preset training conditions are met, and the trained neural network model is obtained. In other words, if the preset neural network model meets the preset training conditions, the trained neural network model is obtained. If the preset neural network model does not meet the preset training conditions, return to step S03 until the preset neural network model meets the preset training conditions, and the trained neural network model is obtained.

In an implementation manner of the embodiment of the present disclosure, a preset loss function value of the neural network model is determined according to the predicted training generated quality data and the actual quality data, and the preset loss function value is compared to the preset loss function value according to the loss function value. The model parameters of the neural network model are corrected. A gradient-based method is used to modify the parameters of the preset neural network model, and after the loss function value of the preset neural network model is determined, the gradient of the parameters of the network model, the parameters of the preset neural network model, and the preset learning rate are calculated according to the loss function value to determine the modified parameters of the preset neural network model.

The preset training conditions include: the loss function value meets a preset requirement and/or the preset number of times of training of the neural network model reaches a preset number of times.

The preset requirement is determined according to the accuracy and efficiency of the preset neural network model, for example, the loss function value of the preset neural network model reaches a minimum value or no longer changes. A preset number of times is the preset maximum number of training times of the neural network model, for example, 4000 times.

The loss function of the preset neural network model includes: a mean square error, a root mean square error, a mean absolute error, etc.

In an implementation manner of the embodiment of the present application, the preset neural network model includes: a feature extraction module and a fully connected module.

For example, the preset neural network model includes: a first convolution unit, a second convolution unit, a third convolution unit, a fourth convolution unit, and a fully connected unit. The first convolution unit includes: two convolution layers and one pooling layer. The second convolution unit, the third convolution unit, and the fourth convolution unit each includes three convolution layers and one pooling layer. The fully connected unit includes three fully connected layers.

The convolutional layer and the fully connected layer are responsible for mapping and transforming an input data. This process uses parameters such as weights and biases, and requires the use of activation functions. The pooling layer is a fixed function operation. The convolutional layer plays a role in extracting features; the pooling layer per-forms a pooling operation on the input features to change their spatial size; and the fully connected layer connects all the data in a previous layer.

In some embodiments, in step S03, the preprocessed training data is input into a preset neural network model, and the predicted training generated quality data corresponding to the preprocessed training data is obtained through the preset neural network model, include:

S031 Inputting the preprocessed training data into the feature extraction module, and obtaining the feature vector corresponding to the preprocessed training data through the feature extraction module;

S032. Inputting the feature vector to the fully connected module, and obtaining the predicted training generated quality data corresponding to the preprocessed training data through the fully connected module.

The preprocessed training data is input into a preset neural network model, and the feature vector corresponding to the preprocessed training data is output through the feature extraction module in the preset neural network model, and the feature vector is input to the fully connected module, and the predicted training generated quality data corresponding to the preprocessed training data output by the fully connected module is obtained.

Figure 3:
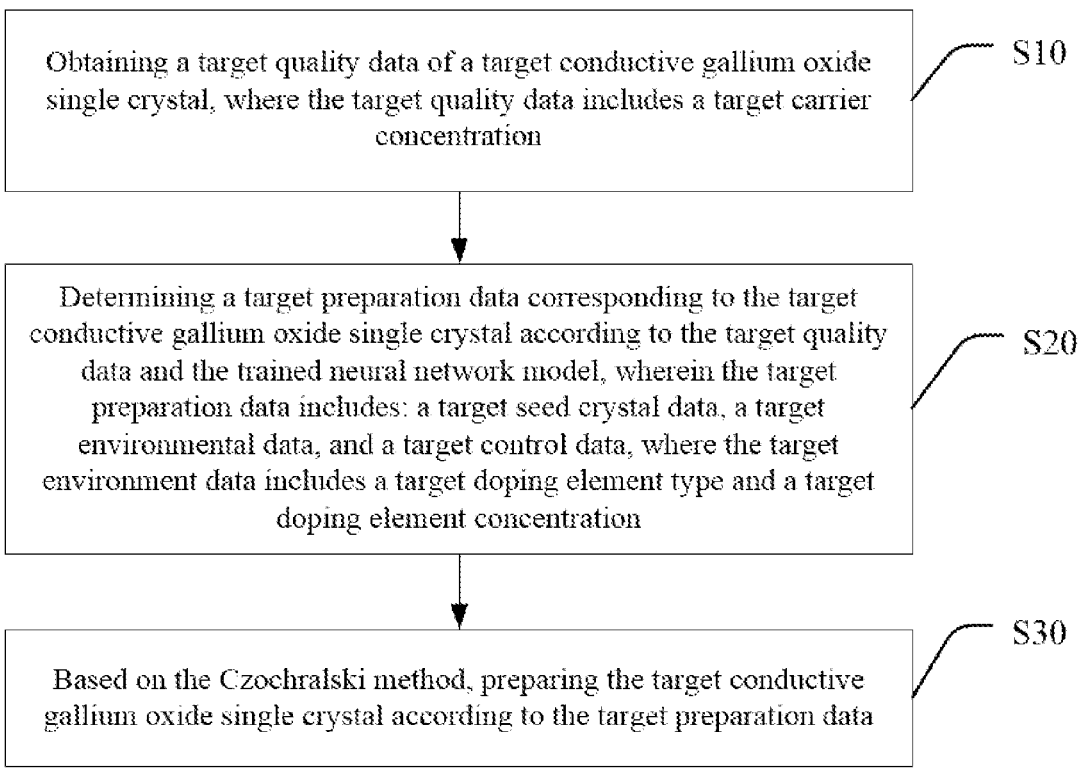
FIG. 3 is a flowchart of an embodiment of a preparation method of conductive gallium oxide based on deep learning and a Czochralski method provided by the present application.

Based on the above-mentioned quality prediction method of conductive gallium oxide based on deep learning and Czochralski method, this embodiment provides a preparation method of conductive gallium oxide based on deep learning and Czochralski method. As shown in FIG. 3, the preparation method includes:

S10. Obtaining a target quality data of a target conductive gallium oxide single crystal, where the target quality data includes a target carrier concentration.

If the target conductive gallium oxide single crystal needs to be obtained, the target quality data of the target conductive gallium oxide single crystal can be determined first, that is, the quality data of the desired conductive gallium oxide single crystal can be determined. The target quality data also includes: a target carrier concentration, a radial deviation value of the target carrier concentration, an axial deviation value of the target carrier concentration, a target crack data, a target impurity data, a half-height width of target diffraction peak, a radial deviation of the target diffraction peak at half maximum width and the axial deviation of the target diffraction peak at half maximum width.

S20. Determining a target preparation data corresponding to the target conductive gallium oxide single crystal according to the target quality data and the trained neural network model, wherein the target preparation data includes: a target seed crystal data, a target environmental data, and a target control data, where the target environment data includes a target doping element type and a target doping element concentration.

The target preparation data corresponding to the target conductive gallium oxide single crystal is determined according to the target quality data and the trained neural network model. It should be noted that since different preparation data can obtain the same quality data, when determining the target preparation data corresponding to the target conductive gallium oxide single crystal according to the target quality data and the trained neural network model, the target preparation data is not unique. A target preparation data is determined according to the control difficulty of each data in the multiple target preparation data, so as to facilitate obtaining the target conductive gallium oxide single crystal.

In some embodiments, the step S20, determining the target preparation data corresponding to the target conductive gallium oxide single crystal according to the target quality data and the trained neural network model, includes:

S21. Obtaining preset preparation data, preprocess the preset preparation data, and obtain preprocessed preset preparation data;

S22. Inputting the preprocessed preset preparation data into a trained neural network model, and obtaining a predicted quality data corresponding to the preprocessed preset preparation data through the trained neural network model;

S23. Correcting the preset preparation data according to the predicted quality data and the target quality data to obtain target preparation data corresponding to the target conductive gallium oxide single crystal.

The preparation data may be preset, and the preset preparation data may be preprocessed to obtain the preprocessed preset preparation data. For the specific preprocessing process, please refer to step S200. The pre-processed preset preparation data is input into the trained neural network model to obtain the predicted quality data that modifies the preprocessed preset preparation data. Then, the preset preparation data can be adjusted according to the predicted quality data and the target quality data. The data is corrected, and when a difference between the predicted quality data and the target quality data is less than a preset threshold, a corrected preset preparation data can be used as the target preparation data.

S30. Based on the Czochralski method, preparing the target conductive gallium oxide single crystal according to the target preparation data.

After obtaining the target preparation data, the Czochralski method can be used to prepare the target conductive gallium oxide single crystal according to the target preparation data.

Figure 4:
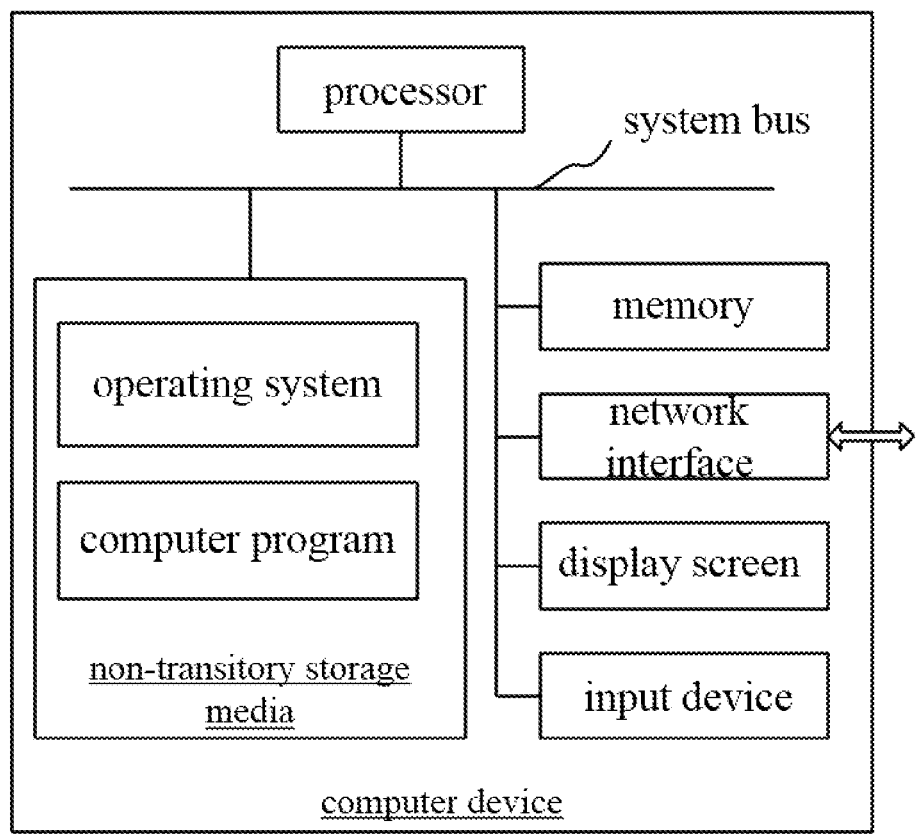
FIG. 4 is a diagram of the internal structure of a conductive gallium oxide preparation system based on deep learning and a Czochralski method provided by the present application.

Based on the above prediction method or the above preparation method, the present disclosure provides a conductive gallium oxide preparation system based on the deep learning and the Czochralski method. The system may be a computer device, and an internal structure is shown in FIG. 4. The system includes a processor, a memory, a network interface, a display screen and an input device connected via a system bus. Among them, the processor of the system is used to provide calculation and control capabilities. The memory of the system includes a non-transitory storage media and an internal memory. The non-transitory storage media stores an operating system and a computer program. The internal memory provides an environment for the operation of the operating system and computer programs in the non-transitory storage media. The network interface of the system is used to communicate with external terminals through a network connection. The computer program is executed by the processor to realize the prediction method of conductive gallium oxide based on deep learning and Czochralski method or the preparation method of conductive gallium oxide based on the deep learning and the Czochralski method. The display screen of the system can be a liquid crystal display screen or an electronic ink display screen, and the input device of the system can be a touch layer covered on the display screen, or a button, a trackball or a touchpad set on the system shell, or it is an external keyboard, a touchpad, or a mouse, etc.

Those skilled in the art can understand that the block diagram shown in FIG. 4 is only a part of the structure related to the solution of the present application, and does not constitute a limitation on the system to which the solution of the present application is applied. The specific system may include those shown in the figure. Show more or fewer components, or combine certain components, or have different component arrangements.

In one embodiment, a conductive gallium oxide preparation system based on the deep learning and the Czochralski method is provided, which includes a memory and a processor, the memory has a computer program stored, and the processor executes the computer program to operate the steps of the prediction method, or the steps of the preparation method.

Finally, it should be noted that the above embodiments are only used to illustrate the technical solutions of the present disclosure, not to limit them; although the present disclosure has been described in detail with reference to the foregoing embodiments, those of ordinary skill in the art should understand that: The technical solutions recorded in the foregoing embodiments are modified, or some of the technical features thereof are equivalently replaced; these modifications or replacements do not cause the essence of the corresponding technical solutions to deviate from the spirit and scope of the technical solutions of the embodiments of the present disclosure.

What is claimed is:

1. A quality prediction and preparation method of conductive gallium oxide based on deep learning and Czochralski method, comprising:
    preparing a seed crystal in a crucible by the Czochralski method;
    determining preparation data of a conductive gallium oxide single crystal prepared by the Czochralski method, the preparation data comprising seed crystal data measured from the seed crystal, an environmental data, and a control data, and the environmental data comprises a doping element concentration and a doping element type;
    preprocessing the preparation data to obtain a preprocessed preparation data and training data;
    training a neural network model using the training data;
    inputting the preprocessed preparation data into a-the trained neural network model;
    determining, by the trained neural network model, a targeted quality data corresponding to the conductive gallium oxide single crystal through the trained neural network model, and the targeted quality data comprises a predicted carrier concentration; and
    preparing a targeted conductive gallium oxide crystal according to the targeted quality data.

2. The quality prediction and preparation method of conductive gallium oxide based on deep learning and the Czochralski method according to claim 1, wherein the preprocessing of the preparation data to obtain the preprocessed preparation data comprises:
    obtaining the preprocessed preparation data according to the seed crystal data, the environmental data, and the control data, and the preprocessed preparation data is a matrix formed by the seed crystal data, the environmental data, and the control data.

3. The quality prediction and preparation method of conductive gallium oxide based on deep learning and the Czochralski method according to claim 2, wherein the seed crystal data comprises a half-height width of seed crystal diffraction peak, a deviation value of the half-height width of seed crystal diffraction peak and a seed crystal diameter;
    the environmental data also comprises a thermal resistance value of a upper insulation cover, a deviation value of the thermal resistance value of the upper insulation cover, a shape factor of a crystal growth channel, a shape factor of a crystal growth observation hole, a thermal resistance value of a lower insulation cover, and a deviation value of the thermal resistance value of the lower thermal insulation cover, a relative height between the crucible and the induction coil, and a relative height between the heating ring and the induction coil; and
    the control data comprises a heating power, a cooling power, an atmosphere type, a cavity pressure, a gas flow rate, a seed crystal rod Czochralski speed, a crystal rotation speed, a crystallizing rate, and a crystal to crucible diameter ratio.

4. The quality prediction and preparation method of conductive gallium oxide based on deep learning and the Czochralski method according to claim 3, wherein the obtaining of the preprocessed preparation data according to the seed crystal data, the environmental data, and the control data comprises:
    determining a preparation vector according to the seed crystal data, the environmental data, and the control data; a first element in the preparation vector is one of the half-height width of seed crystal diffraction peak, the deviation value of the half-height width of seed crystal diffraction peak and the seed crystal diameter; a second element in the preparation vector is one of a concentration of a doping element, a type of the doping element, a thermal resistance value of the upper insulation cover, the deviation value of the thermal resistance value of the upper insulation cover, the shape factor of the crystal growth channel, the shape factor of the crystal growth observation hole, the thermal resistance value of the lower insulation cover, the deviation value of the thermal resistance value of the lower insulation cover, the relative height between the crucible and the induction coil, and the relative height between the heating ring and the induction coil; a third element in the preparation vector is one of the heating power, the cooling power, the atmosphere type, the cavity pressure, the gas flow rate, the seed rod Czochralski speed, the crystal rotation speed, the crystallization rate, and the crystal to crucible diameter ratio; and
    determining the preprocessed preparation data according to the preparation vector.

5. The quality prediction and preparation method of conductive gallium oxide based on deep learning and the Czochralski method according to claim 1, wherein the predicting quality data further comprises: a predicted crack data, a predicted hybrid crystal data, a half-height width of predicted diffraction peak , a radial deviation value of the half-height width of predicted diffraction peak , a axial deviation value of the half-height width of predicted diffraction peak , a radial deviation value of the predicted load of carrier concentration, and an axial deviation value of the predicted carrier concentration.

6. The quality prediction and preparation method of conductive gallium oxide based on deep learning and the Czochralski method according to claim 1, wherein the trained neural network model is trained by:
    obtaining a training data and corresponding actual quality data for preparing conductive gallium oxide single crystal by the Czochralski method, the training data comprises comprising a seed crystal training data, an environmental training data, and a control training data;
    preprocessing the training data to obtain preprocessed training data;
    inputting the preprocessed training data into a preset neural network model, and obtaining a predicted training generated quality data corresponding to the preprocessed training data through the preset neural network model; and adjusting and correcting model parameters of the preset neural network model according to the predicted training generated quality data and the actual quality data to obtain a trained neural network model.

7. The quality prediction and preparation method of conductive gallium oxide based on deep learning and the Czochralski method according to claim 6, wherein the preset neural network model comprises a feature extraction module and a fully connected module, the step of inputting the preprocessed training data into a preset neural network model, and obtaining the predicted training generated quality data corresponding to the preprocessed training data through the preset neural network model comprises:

inputting the preprocessed training data into the feature extraction module, and obtaining a feature vector corresponding to the preprocessed training data through the feature extraction module; and inputting the feature vector into the fully connected module, and obtaining the predicted training generated quality data corresponding to the preprocessed training data through the fully connected module.

8. A preparation method of conductive gallium oxide based on deep learning and Czochralski method, comprising:

preparing a seed crystal in a crucible by the Czochralski method;

determining a target quality data of a target conductive gallium oxide single crystal, the target quality data comprising a target carrier concentration;

determining the target preparation data corresponding to the target conductive gallium oxide single crystal according to the target quality data and a trained neural network model, the target preparation data comprising target seed data measured from the prepared seed crystal, a target environment data, and a target control data, the target environment data comprises a target doping element concentration and a target doping element type, wherein the trained neural network is trained with a training set; and preparing, based on the Czochralski method, the target conductive gallium oxide single crystal according to the target preparation data.

9. The preparation method of conductive gallium oxide based on deep learning and Czochralski method according to claim 8, the determining the target preparation data corresponding to the target conductive gallium oxide single crystal according to the target quality data and the trained neural network model, comprises steps:

acquiring a preset preparation data, preprocessing the preset preparation data, and obtaining the preprocessed preset preparation data;

inputting the preprocessed preset preparation data into a trained neural network model, and obtaining a predicted quality data corresponding to the preprocessed preset preparation data through the trained neural network model; and correcting the preset preparation data according to the predicted quality data and the target quality data to obtain the target preparation data corresponding to the target conductive gallium oxide single crystal.

10. A conductive gallium oxide preparation system based on deep learning and Czochralski method, comprising a non-transitory memory and a processor, and a computer program is stored in the non-transitory memory, wherein the processor executes the computer program to operate the steps of the prediction method according to claim 1.

* * * * *